United States Patent
Agnaou et al.

(10) Patent No.: US 12,076,423 B2
(45) Date of Patent: Sep. 3, 2024

(54) SPICULISPORIC ACID-BASED COMPOSITION

(71) Applicant: L'OREAL, Paris (FR)

(72) Inventors: Reda Agnaou, Chevilly Larue (FR); Catherine Marion, Chevilly Larue (FR)

(73) Assignee: L'OREAL, Paris (FR)

( * ) Notice: Subject to any disclaimer, the term of this patent is extended or adjusted under 35 U.S.C. 154(b) by 1037 days.

(21) Appl. No.: 16/065,255

(22) PCT Filed: Dec. 23, 2016

(86) PCT No.: PCT/EP2016/082590
§ 371 (c)(1),
(2) Date: Jun. 22, 2018

(87) PCT Pub. No.: WO2017/109192
PCT Pub. Date: Jun. 29, 2017

(65) Prior Publication Data
US 2021/0205185 A1   Jul. 8, 2021

(30) Foreign Application Priority Data

Dec. 23, 2015   (FR) ........................................ 1563240
Dec. 23, 2015   (FR) ........................................ 1563245

(51) Int. Cl.
| | |
|---|---|
| *A61K 8/06* | (2006.01) |
| *A61K 8/41* | (2006.01) |
| *A61K 8/44* | (2006.01) |
| *A61K 8/49* | (2006.01) |
| *A61K 8/73* | (2006.01) |
| *A61K 8/92* | (2006.01) |
| *A61Q 17/00* | (2006.01) |
| *A61Q 19/00* | (2006.01) |

(52) U.S. Cl.
CPC ................ *A61K 8/062* (2013.01); *A61K 8/41* (2013.01); *A61K 8/44* (2013.01); *A61K 8/4973* (2013.01); *A61K 8/73* (2013.01); *A61K 8/92* (2013.01); *A61Q 17/00* (2013.01); *A61Q 19/00* (2013.01); *A61K 2800/30* (2013.01); *A61K 2800/48* (2013.01); *A61K 2800/524* (2013.01)

(58) Field of Classification Search
None
See application file for complete search history.

(56) References Cited

U.S. PATENT DOCUMENTS

| | | | | |
|---|---|---|---|---|
| 2003/0039671 | A1* | 2/2003 | Tournilhac | A61K 8/11 424/401 |
| 2008/0311234 | A1* | 12/2008 | Yoneda | A61Q 19/00 424/780 |

FOREIGN PATENT DOCUMENTS

| | | | | |
|---|---|---|---|---|
| EP | 1184426 | A2 | 3/2002 | |
| FR | 2679771 | A1 | 2/1993 | |
| JP | H0559389 | A | 3/1993 | |
| JP | 2000191789 | A | 7/2000 | |
| JP | 2003128788 | A | 5/2003 | |
| WO | 2007068371 | A1 | 6/2007 | |
| WO | 2008155059 | A2 | 12/2008 | |
| WO | 2008155059 | A3 | 12/2008 | |
| WO | 2015067784 | A1 | 5/2015 | |
| WO | 2015067785 | A1 | 5/2015 | |
| WO | WO-2015067779 | A1 * | 5/2015 | ............... A61K 8/06 |
| WO | 2016-005707 | A1 | 1/2016 | |
| WO | WO-2016005209 | A1 * | 1/2016 | ............. A61K 8/362 |

OTHER PUBLICATIONS

PubChem Arginine., https://pubchem.ncbi.nlm.nih.gov/compound/6322, retrieved online Dec. 15, 2021 (Year: 2021).*
PubChem Spiculisporic Acid, https://pubchem.ncbi.nlm.nih.gov/compound/316426, retrieved online Dec. 15, 2021 (Year: 2021).*
Lefebvre, M.A. et al., "Evaluation of the impact of urban pollution on the quality of skin: a multicentre study in Mexico", International Journal of Cosmetic Science, vol. 37, Issue 3, Jun. 2015, 329-338.
International Search Report of PCT International App. No. PCT/EP2016/082590 dated Jun. 19, 2017 with English Translation (7 pages).
Written Opinion of the International Search Authority of PCT International App. No. PCT/EP2016/082590 dated Jun. 19, 2017 with English Translation (25 pages).

* cited by examiner

*Primary Examiner* — Jennifer A Berrios
(74) *Attorney, Agent, or Firm* — Shumaker, Loop & Kendrick, LLP

(57) ABSTRACT

Composition in the form of an oil-in-water emulsion that includes at least 1% of an oil phase, and an aqueous phase. The composition includes 0.1 to 15 wt % spiculisporic acid relative to the total weight of the composition, at least one base selected from amino acids and alkanolamines in an amount suitable for forming at least a monosalt of spiculisporic acid, less than 3% glycol(s) and/or polyol(s) relative to the total weight of the composition, at least one UV filter and/or an additive selected from volatile aromatic materials such as essential oils and fragrance substances, fillers, dyeing materials such as pigments, mother-of-pearl or particles with a metallic sheen, moisturizers, anti-wrinkle or anti-age agents, peeling agents, antioxidants, active ingredients stimulating the synthesis of epidermal and/or dermal macromolecules, dermo-relaxing agents, depigmentation agents, deodorant agents and mixtures thereof.

13 Claims, No Drawings

SPICULISPORIC ACID-BASED COMPOSITION

TECHNICAL FIELD AND BACKGROUND

The present invention relates to the field of film-forming compositions that can be used in the cosmetics industry; more particularly, the invention is directed toward emulsions with film-forming properties.

The production of compositions that are capable of forming a stable homogeneous film is a recurrent technical problem in many fields and more particularly in the cosmetics industry, for instance for applications as creams, deodorants, mascaras, nail varnishes, care products and/or makeup products.

Specifically, by virtue of this film-forming property, many cosmetic products will experience an improvement in their properties, whether in terms of dispersion of the components, of feel or else of barrier effect between the support onto which the composition has been applied and the external medium.

Generally, in order to obtain compositions of this type, conventional film-forming polymers are mainly used: in addition, when it is intended to obtain an emulsion, synthetic surfactant molecules with a film-forming property, generally derived from petroleum, are preferably used.

However, most of the petroleum-based synthetic surfactant molecules with a film-forming property that are used in the various industries are harmful to the environment.

Furthermore, synthetic surfactants are, admittedly, good emulsifiers, but most of them result in the formation of films that are moisture-sensitive and sparingly cohesive. There consequently remains a need for film-forming emulsifying systems that are environmentally friendly.

Moreover, the human skin and scalp are the first barriers protecting the body against the environment. Each day, they are subject to external attacking factors, which are responsible for many skin problems, such as accelerated aging, skin ailments, discomfort, or the greasy condition of the skin, etc.

In particular, atmospheric pollution, namely the amount of pollutants in the air, is raising an increasing number of concerns for consumers, owing to its negative impact on the skin. Among the various types of pollutants that are present in the air, dust or fine particles, such as particles with a diameter of less than 10 µm (PM10), preferably less than 2.5 µm (PM2.5), carbon powders, and gases such as CO, $SO_2$ or $NO_x$, have attracted consumer attention, in particular in the last few years.

The fine particles that are present in the air tend to adhere to the skin. They become deposited or remain deposited on the skin even after cleansing. This deposition is not desired by consumers, since it is thought that the skin pores can be blocked, thus resulting in skin problems. Atmospheric pollution is also responsible for problems of skin aging (in particular associated with oxidative stress generated by pollutant particles, UV radiation, tobacco, etc.), of dehydrated skin or else of an increase in seborrhea (Lefebvre et al., 2015, International Journal of Cosmetic Science, 37: 329-338).

The prior art does not disclose any solutions for preventing or reducing the deposition of fine particles on the skin and the scalp.

There is thus a considerable need for the preparation of compositions which have an anti-deposition effect against fine particles. More particularly, there is a need for compositions which have beneficial anti-deposition properties in addition to other properties, for instance moisturizing properties or improved softness properties, after application to keratin materials, in particular to the skin or the scalp. It is also advantageous for such compositions to be capable of having the effects described above for a relatively long period of time, for example for 6 to 8 hours.

Cosmetic compositions often comprise volatile components such as volatile solvents in the aqueous phase of care or makeup compositions, volatile oils in makeup compositions or, for certain applications, essential oils.

However, their volatility may pose a certain number of problems.

Specifically, when the desired effect is not associated with the volatility of the compound, it is often desired to reduce this volatility in order to dispense with the need to introduce an excessive amount of volatile materials into the products comprising same, and especially into cosmetic and/or dermatological compositions.

As more particularly regards essential oils, they are generally odorous but not always fragrancing: specifically, they do not always generate an odor that is pleasant to those in the vicinity. They are used in a wide variety of food, deodorizing and cosmetic products. Their complex composition offers them specific biological properties according to the origin of the plant, such as antiaging, antibacterial, deodorant, etc. properties.

However, the constituents of these plant-based active agents are essentially hydrophobic and are volatile to a greater or lesser extent which generally makes them difficult to formulate.

SUMMARY

Thus, in this context, it would be desirable to reduce the volatility of the odorous volatile materials. This would advantageously make it possible, firstly, to conserve a larger amount of said volatile material at its site of application and thus to increase its efficacy, and, secondly, to reduce the cost price of compositions containing same.

The authors of the present invention have shown that these problems can be solved by using particular spiculisporic acid salts.

Spiculisporic acid is an emulsifying biosurfactant derived from a microorganism, which is nontoxic to the environment.

Consequently, this biosurfactant appears to be an advantageous alternative to petroleum-based synthetic surfactant molecules with a film-forming property insofar as the latter are generally harmful to the environment.

Furthermore, synthetic surfactants are, admittedly, good emulsifiers, but most of them result in the formation of films that are moisture-sensitive and sparingly cohesive.

DETAILED DESCRIPTION

Thus, the present invention relates to a composition, in particular a cosmetic composition, in the form of an oil-in-water emulsion comprising an oily phase, an aqueous phase characterized in that it comprises:

- from 0.1% to 15%, preferably from 0.5% to 10% and even more preferably from 0.7% to 8% by weight of spiculisporic acid relative to the total weight of the composition,
- at least one base chosen from amino acids and alkanolamines in an amount capable of forming at least the monosalt of spiculisporic acid, said composition comprising less than 3%, preferably less than 1% by weight of glycol(s) and/or of polyol(s) relative to the total weight of the composition, the composition being advantageously free of glycols and/or polyols.

More particularly, the present invention relates to a composition, in particular a cosmetic composition, in the form of an oil-in-water emulsion comprising at least 1% of an oily phase, and an aqueous phase characterized in that it comprises:

from 0.1% to 15%, preferably from 0.5% to 10% and even more preferably from 1% to 8% by weight of spiculisporic acid relative to the total weight of the composition, at least one base chosen from amino acids and alkanolamines in an amount capable of forming at least the monosalt of spiculisporic acid, less than 3%, preferably less than 1% by weight of glycol(s) and/or polyol(s) relative to the total weight of the composition, and advantageously being free of glycols and/or polyol(s), at least one UV-screening agent and/or one additive chosen from odorous volatile materials such as essential oils and fragrancing substances, fillers, dyestuffs such as pigments, nacres or particles with a metallic tint, moisturizers, antiwrinkle or antiaging agents, desquamating agents, antioxidants, active agents for stimulating the synthesis of dermal and/or epidermal macromolecules, dermo-decontracting agents, depigmenting agents and deodorants, and mixtures thereof.

The composition according to the invention is capable of forming a stable, homogeneous and resistant film on keratin materials. The compositions of the invention thus have increased anti-deposition properties against fine particles, in particular via the formation of antiadhesive films on keratin materials, making it possible to prevent the deposition of pollutant compounds on said keratin materials.

The components used especially have fatty phase film-forming properties and make it possible to stabilize a film that can be described as a "fatty film".

In one particular embodiment, the compositions according to the invention also comprise from 0.0001% to 30% of at least one odorous volatile material chosen from essential oils and fragrancing substances, preferably essential oils.

The composition in accordance with the invention advantageously makes it possible to reduce the volatility of an odorous volatile material, in particular of an essential oil, while at the same time reducing its impairment.

The compositions according to the invention thus make it possible to limit or even prevent the evaporation of said odorous volatile material.

The present invention thus aims to provide compositions intended to be used for caring for and/or making up keratin materials, having improved properties of resistance to dust and to fine particles, that is to say having an effect acting against the deposition of fine particles on keratin materials.

Consequently, the use of spiculisporic acid in the context of the invention also makes it possible to dispense with the addition of additional film-forming polymers. Indeed, it is always advantageous to be able to formulate compositions comprising a limited number of ingredients.

Furthermore, the emulsifying properties of this biosurfactant are at least of the order of those of synthetic surfactants: the O/W emulsions according to the invention are consequently particularly stable and homogeneous, as shown in the examples hereinafter.

The composition according to the invention constitutes an advantageous alternative to the prior art compositions comprising synthetic surfactants by virtue of its emulsifying capacity, and by virtue of the stability, the persistence and the moisture resistance of the films obtained after drying said composition.

The composition according to the invention is also particularly environmentally friendly.

The composition according to the invention also has the advantage of being able to be formulated by integrating the appropriate ingredients for very diverse cosmetic applications such as deodorants, mascaras, nail varnishes, care and/or makeup products, such as creams, foundations or haircare products, and in particular products containing odorous volatile materials such as fragrances or, advantageously, essential oils.

The compositions obtained, in particular the care and/or makeup products, also lead to films which have advantages in terms of sensory properties, in particular a pleasant feel.

The film obtained by applying the care and/or makeup compositions undergoes quick breaking, but this film nevertheless acts as a drag upon spreading. This property of acting as a drag upon application leads the consumer to apply said composition for a longer period of time and with greater pressure on the skin, thereby enabling better penetration of the active agents. Disappearance of the drag can also constitute a sign of complete and successful application.

According to a second aspect, the present invention targets the use of the composition according to the invention as a makeup, care, hygiene and/or cleansing product for keratin materials, in particular the skin or the hair, in particular as a cleansing product for keratin materials.

According to a third aspect, the present invention targets a nontherapeutic cosmetic makeup, care, hygiene and/or cleansing process comprising a step of applying the composition according to the invention to said keratin materials.

More particularly, the composition according to the invention is a composition for protecting keratin materials, more particularly the skin, against atmospheric pollutants.

Thus, the present invention also targets the use of the composition according to the invention for protecting keratin materials against atmospheric pollutant compounds chosen in particular from carbon black, carbon oxides, nitrogen oxides, sulfur oxides, hydrocarbon-based compounds, volatile organic compounds, heavy metals, PM2.5 and PM10 fine particles, and mixtures thereof.

More particularly, said use is directed toward protecting keratin materials against disorders caused by atmospheric pollutant compounds, said disorders being chosen from greasy skin, skin dehydration, desquamation impairment, a decrease in squalene, a decrease in vitamin E, pigmentation and an increase in lactic acid.

The present invention is also directed toward a nontherapeutic cosmetic process for protecting keratin materials against atmospheric pollutant compounds in particular chosen from carbon black, carbon oxides, nitrogen oxides, sulfur oxides, hydrocarbon-based compounds, volatile organic compounds, heavy metals, PM2.5 and PM10 fine particles, and mixtures thereof comprising a step of applying the composition according to the invention to said keratin materials.

More particularly, said process is directed toward protecting keratin materials against disorders caused by atmospheric pollutant compounds, said disorders being chosen from greasy skin, skin dehydration, desquamation impairment, a decrease in squalene, a decrease in vitamin E, pigmentation and an increase in lactic acid.

The present invention is also directed toward the use of spiculisporic acid in a form partially or totally neutralized with a base chosen from amino acids and alkanolamines in a composition, in particular a cosmetic composition, as a film-forming agent for forming a film on the surface of keratin materials, especially on the skin or the hair: more particularly, this use is such that the film formed protects the keratin materials against atmospheric pollutant compounds or such that the film formed promotes homogeneous distribution of at least one active agent included in the composition on the keratin materials, said active agent preferentially being a UV-screening agent, which is preferably lipophilic, and/or an additive chosen from fillers, dyestuffs such as pigments, nacres or particles with a metallic tint, moisturizers, antiwrinkle or antiaging agents, desquamating agents, antioxidants, active agents for stimulating the synthesis of dermal and/or epidermal macromolecules, dermo-decontracting agents, depigmenting agents and deodorants, and mixtures thereof.

The present invention is also directed toward the use of spiculisporic acid in a form partially or totally neutralized with a base chosen from amino acids and alkanolamines, for preventing and/or limiting and/or avoiding the evaporation of an odorous volatile material contained in a cosmetic composition.

Finally, the present invention is also directed toward the use of spiculisporic acid in the form of a monosalt of a base chosen from amino acids and alkanolamines, for preventing and/or limiting and/or avoiding the evaporation of an odorous volatile material contained in a cosmetic composition.

Other variants, advantages and properties of the invention will be demonstrated in the description and the examples that follow.

Spiculisporic Acid

The composition in emulsion form according to the invention comprises spiculisporic acid, also known as 4,5-dicarboxy-4-pentadecanolide, of formula:

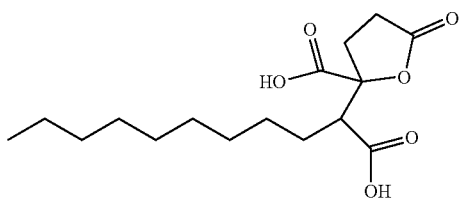 [SMILES: CCCCCCCCCC(C(=O)O)C1(C(=O)O)CCC(=O)O1]

It is known that spiculisporic acid, also referred to as "Sp acid" in the remainder of the text, is insoluble, at room temperature, in water and fatty substances, but that it is soluble in ethanol.

In addition, it is known that spiculisporic acid can be dissolved, at room temperature, by salification.

More exactly, Sp acid can form a monosalt, a disalt or a trisalt.

The monosalt corresponds to the product of neutralization of the carboxylic group bonded to the carbon atom in position C4 of Sp acid:
 the disalt corresponds to the product of neutralization of the carboxylic groups bonded to the carbon atoms in positions C4 and C5 of Sp acid;
 the trisalt corresponds to the product of neutralization of the carboxylic groups bonded to the carbon atoms in positions C4 and C5 of Sp acid and of salification of the lactone function in its open form.

In the emulsions according to the invention, spiculisporic acid may be in the form of a monosalt, a disalt or a trisalt or a mixture of several salts with a different degree of salification.

According to a preferred embodiment of the invention, spiculisporic acid is in the form of a monosalt.

As already mentioned, the amount of spiculisporic acid ranges from 0.1% to 15%, preferably from 0.5% to 10% and even more preferably from 0.7% to 8% by weight of spiculisporic acid relative to the total weight of the composition.

In particular, the amount of spiculisporic acid is 0.6, 0.7, 0.8, 0.9, 1.0, 1.1, 1.2, 1.3, 1.4, 1.5, 2, 3, 4, 5, 6, 7, 8, 9 or 10% by weight relative to the total weight of the composition.

Base

The emulsion according to the present invention comprises at least one base chosen from amino acids and alkanolamines, said base being present in an amount capable of forming at least the monosalt of spiculisporic acid.

The base used is a neutralizing base, i.e. it enables spiculisporic acid to be neutralized so as to form a salt of said acid.

The base(s) are thus used in an amount that is capable of forming the monosalt, the disalt, the trisalt or a mixture of several salts of spiculisporic acid with different degrees of salification.

According to a preferred embodiment of the invention, the amount of base is chosen so as to form the monosalt of spiculisporic acid.

In the context of the invention, the base is chosen from amino acids and alkanolamines.

More particularly, the base may be chosen from the following basic amino acids: arginine, lysine, ornithine, citrulline and histidine. The amino acid is preferably arginine.

The base may also be chosen from the following alkanolamines: mono-, di- and triethanolamines, isopropanolamine and 2-amino-2-methyl-1-propanol, and also mixtures thereof. Preferably, the alkanolamine is triethanolamine.

Advantageously, the amount of base ranges from 0.1% to 20%, preferably from 0.5% to 15% and even more preferably from 0.6% to 10% by weight relative to the total weight of the composition.

Physiologically Acceptable Medium

Besides the compounds indicated previously, a composition according to the invention comprises a physiologically acceptable medium.

The term "physiologically acceptable medium" is intended to denote a medium that is particularly suitable for applying a composition of the invention to the skin and/or the lips, for instance water or the oils or organic solvents commonly used in cosmetic compositions.

The physiologically acceptable medium (acceptable tolerance, toxicology and feel) is generally adapted to the nature of the support onto which the composition is to be applied, and also to the form in which the composition is to be conditioned.

Oily Phase

The composition in accordance with the invention may comprise an oily phase, also known as a fatty phase.

As shown in the examples, the composition may contain up to 70% and preferably up to 60% by weight of fatty phase relative to the total weight of the composition. The compositions, even comprising a large amount of fatty phase, can produce films that are stable, homogeneous and resistant.

The fatty phase of the composition according to the invention comprises all of the liposoluble or lipodispersible compounds present in the composition, and in particular the fatty substances that are liquid at room temperature)(25° ° C. and atmospheric pressure or oils (which form the oily phase).

The oils present in the composition in accordance with the invention may be silicone oils or hydrocarbon-based oils.

The term "silicone oil" means an oil containing at least one silicon atom, and especially containing Si—O groups.

Examples of silicone oils that may be mentioned include volatile silicone oils such as cyclopoly dimethylsiloxanes (INCI name: cyclomethicone), such as cyclopentasiloxane, cyclohexasiloxane, octamethylcyclotetrasiloxane, decamethylcyclopentasiloxane, dodecamethylcyclohexasiloxane: linear silicones such as heptamethy lhexyltrisiloxane, heptamethyloctyltrisiloxane, hexamethyldisiloxane, octamethyltrisiloxane, decamethyltetrasiloxane or dodecamethylpentasiloxane: nonvolatile silicone oils such as polymethylsiloxanes (PDMS), and phenyl polymethylsiloxanes such as phenyl trimethicones, phenyl dimethicones, phenyltrimethylsiloxy diphenylsiloxanes, diphenyl dimethicones, diphenylmethyldiphenyltrisiloxanes, 2-phenylethyl trimethyl siloxysilicates and polymethylphenylsiloxanes: polysiloxanes modified with fatty acids, fatty alcohols or polyoxyalkylenes, and mixtures thereof.

The term "volatile" refers to a compound that can evaporate on contact with the skin in less than one hour, at room temperature and atmospheric pressure. The volatile oil is a volatile cosmetic oil, which is liquid at room temperature, especially having a nonzero vapor pressure, at room temperature and atmospheric pressure, in particular having a vapor pressure ranging from 0.13 Pa to 40 000 Pa (103 to 300 mmHg), preferably ranging from 1.3 Pa to 13 000 Pa (0.01 to 100 mmHg) and preferentially ranging from 1.3 Pa to 1300 Pa (0.01 to 10 mmHg).

The term "hydrocarbon-based oil" means an oil formed essentially from, or even constituted of, carbon and hydrogen atoms, and possibly oxygen and nitrogen atoms, and containing no silicon or fluorine atoms; it may contain ester, ether, amine or amide groups.

As oils that may be used in the composition of the invention, mention may be made, for example, of:
- hydrocarbon-based oils of plant origin, such as squalane, liquid triglycerides of fatty acids comprising from 4 to 30 carbon atoms, for instance heptanoic or octanoic acid triglycerides, or alternatively, for example, jojoba oil, babassu oil, sunflower oil, olive oil, coconut oil, Brazil nut oil, marula oil, corn oil, soy bean oil, marrow oil, grapeseed oil, linseed oil, sesame seed oil, hazelnut oil, apricot oil, macadamia nut oil, arara oil, coriander oil, castor oil, avocado oil, caprylic/capric acid triglycerides, for instance those sold by the company Stearineries Dubois or those sold under the names Miglyol 810, 812 and 818 by the company Dynamit Nobel, and shea butter oil;
- synthetic esters and ethers, in particular of fatty acids, for instance the oils of formulae RICOOR2 and RIOR2 in which R1 represents a fatty acid or fatty alcohol residue containing from 8 to 29 carbon atoms and R2 represents a branched or unbranched hydrocarbon-based chain containing from 3 to 30 carbon atoms, for instance Purcellin oil, 2-octyldodecyl stearate, 2-octyldodecyl erucate or isostearyl isostearate: hydroxylated esters, for instance isostearyl lactate, octyl hydroxystearate, octyldodecyl hydroxystearate, diisostearyl malate or triisocetyl citrate: fatty alcohol heptanoates, octanoates or decanoates: polyol esters, for instance propylene glycol dioctanoate, neopentyl glycol diheptanoate and diethylene glycol diisononanoate; and pentaerythritol esters, for instance pentaerythrityl tetraisostearate;
- volatile or nonvolatile, linear or branched hydrocarbons of mineral or synthetic origin, and derivatives thereof, for instance branched alkanes comprising from 8 to 18 carbon atoms, for example C8-C18 isoalkanes (also called isoparaffins), for instance isododecane, isodecane, isohexadecane, such as the isoparaffins sold under the trade names Isopar by the company Exxon Chemical or the oils sold under the trade names Permethyl by the company Presperse, the isohexadecane and isododecane sold by the company Ineos; and also liquid petroleum jelly and hydrogenated polyisobutene such as Parleam® oil: volatile linear alkanes comprising from 7 to 17 carbon atoms, for instance undecane and tridecane;
- fatty alcohols that are liquid at room temperature, containing from 8 to 26 carbon atoms, for instance octyldodecanol, 2-butyloctanol, 2-hexyldecanol, 2-undecylpentadecanol or oleyl alcohol; and
- mixtures thereof.

Mention may in particular be made of the following oils:
- esters derived from the reaction of at least one fatty acid containing at least 6 carbon atoms, preferably from 6 to 26 carbon atoms, better still from 6 to 20 carbon atoms and even better still from 6 to 16 carbon atoms, and of at least one alcohol comprising from 1 to 17 carbon atoms and better still from 3 to 15 carbon atoms: mention may in particular be made of isopropyl myristate, isopropyl palmitate, 2-ethylhexyl caprate/caprylate (or octyl caprate/caprylate), 2-ethylhexyl palmitate, isostearyl neopentanoate, isononyl isononanoate, hexyl laurate, lactic acid esters of fatty alcohols comprising 12 or 13 carbon atoms, and dicaprylyl carbonate, such as the product which is sold under the name Cetiol CC by the company Cognis,
- fatty acid ethers comprising from 6 to 20 carbon atoms, such as dicaprylyl ether (Cetiol OE from Cognis),
- glycerol ethers comprising from 6 to 12 carbon atoms, for instance the 2-ethylhexyl ether of glycerol (INCI name: ethylhexyl glycerol) such as Sensiva SC 50 from the company Schulke & Mayr GmbH,
- octyldodecanol,
- alkanes such as those which are described in the Cognis patent applications WO2007/068371 or WO2008/155059 (mixtures of distinct alkanes differing by at least one carbon). These alkanes are obtained from fatty alcohols, which are themselves obtained from coconut kernel oil or palm oil.

As examples of linear alkanes that are suitable for use in the invention, mention may be made of n-heptane (C7), n-octane (C8), n-nonane (C9), n-decane (C10), n-undecane (C11), n-dodecane (C12), n-tridecane (C13) and n-tetradecane (C14), and mixtures thereof. According to a particular embodiment, the volatile linear alkane is chosen from n-nonane, n-undecane, n-dodecane, n-tridecane and n-tetradecane, and mixtures thereof.

According to a preferred embodiment, mention may be made of mixtures of n-undecane (C11) and of n-tridecane (C13) obtained in Examples 1 and 2 of patent application WO 2008/155059 by the company Cognis:
- polyesters obtained by condensation of a dimer and/or trimer of an unsaturated fatty acid and of a diol, for instance the polyesters of dilinoleic acid and of diol sold by Biosynthis under the name Viscoplast and in particular the polymer bearing the INCI name dilinoleic acid/propanediol copolymer; and mixtures thereof.

Preferably, the oil is chosen from the plant oils as mentioned above.

The amount of fatty phase in the composition of the invention is at least 1% by weight, preferably at least 5% by weight, and may range from 1% to 70% by weight, preferably from 5% to 70% and preferably from 5% to 60% by weight relative to the total weight of the composition.

After spreading onto the keratin materials and drying, the composition according to the invention advantageously forms a film, and preferably a hydrophilic film, which has high wettability (and thus has a high-energy surface), i.e. it has strong affinity for water.

For the purposes of the invention, the term "wettability" means the ability of a surface to be wetted by a given material, in particular by water. In general, when a liquid is placed in contact with the surface of a solid (in this instance, the film formed), it forms a contact angle of the first on the second. When the wetting is perfect, the contact angle becomes zero. In this case, the adhesion energy is maximal. The wettability is evaluated via methods that are well known to those skilled in the art, consisting essentially in measuring the contact angle of a drop of water placed on the surface of the film formed after spreading the composition and drying. This contact angle, generally known as the alpha angle, corresponds to the angle existing between the surface of the film and the tangent to the drop at the surface/water/air interface. This angle may be between 0° and 180°.

If the angle is zero, then the wetting is total. i.e. the liquid spreads completely over the surface and there are thus strong interactions between the support and the liquid. If the angle is 180°, then the wetting is zero, i.e. the liquid forms a bead. There is only one point of contact between the liquid and the support, and above all no affinity.

For intermediate angles, the wetting is partial. Thus, it is considered that when this contact angle is greater than 45°, then the material has a low-energy surface. Conversely, when this contact angle is less than 45°, then the material has a high-energy surface. In general, low-energy materials are of hydrophobic nature. For the purposes of the invention, the term "surface of hydrophobic nature" refers to a surface characterized by a contact angle of a water drop of greater than or equal to 45° and generally greater than 70°. The term "hydrophilic" is, for its part, used to denote a surface characterized by a contact angle of a water drop of less than 45°, and preferably less than or equal to 30°.

The protocols for evaluating the wetting of the film formed by the compositions according to the invention are well known in the prior art. A protocol for evaluating the wetting may especially be as follows.

The composition according to the invention is applied to the surface of a support, which is preferably flat, said support preferably being a keratin material or any other suitable support, at a temperature of between 15° C. and 50° ° C. (preferably between 19 and 25° C.), under humidity conditions of between 10% and 70%, and preferably between 50% and 60%, and under standard atmospheric pressure conditions. The deposition of the composition onto the surface of the support may advantageously be performed using a film spreader.

The drying is performed, for example, at a temperature of between 15°C' and 50° C. (preferably between 19 and 25° C.), and under humidity conditions of between 10% and 70%, and preferably between 50% and 60%, under standard atmospheric pressure conditions.

The contact angle is then measured 0.1 s after placing a drop of water on the surface of the film.

The wetting may especially be measured by contact angle tensiometry, for example using the tensiometer DAT 1100 sold by the company Fibro (Sweden), or using a standard machine for measuring the contact angle, for instance the SDT-200 machine sold by the company IT Concept, used in static mode, or using an MSA Surface Analyzer sold by the company Krüss.

In a preferred embodiment, the film formed after drying with the compositions according to the invention is characterized in that it is hydrophilic, and has a contact angle of a water drop of less than or equal to 45°, preferably less than or equal to 40°, preferably less than or equal to 35°, even more preferably less than or equal to 30° and preferably less than or equal to 25°.

In a preferred embodiment, the compositions according to the invention do not comprise any film-forming agent or system other than that formed by spiculisporic acid and the base, as described above. In particular, the compositions according to the invention comprise less than 5%, preferably less than 3%, preferably less than 2%, preferably less than 1%, preferably less than 0.5% and even more preferably do not comprise any film-forming agent or system other than that formed by spiculisporic acid and the base, as described above. The term "other film-forming agent or system" preferably means compounds that are capable of forming films, alone or in combination, and in particular pectin, combinations of pectin and of divalent ions, such as calcium carbonate, or film-forming polymers. In a preferred embodiment, the compositions according to the invention do not simultaneously comprise pectin and divalent ions, such as calcium salts and more specifically calcium carbonate. In a preferred embodiment, the compositions according to the invention are free of pectin. In another preferred embodiment, the compositions according to the invention are free of film-forming polymers.

Odorous Volatile Materials

The composition according to the invention advantageously comprises at least one odorous volatile material.

For the purposes of the invention, the term "volatile material" refers to any compound that is capable of evaporating on contact with the skin in less than one hour, at room temperature and atmospheric pressure. The volatile material is a volatile cosmetic compound, which is liquid at room temperature, especially having a nonzero vapor pressure, at room temperature and atmospheric pressure, especially having a vapor pressure ranging from 0.13 Pa to 40 000 Pa (10-3 to 300 mmHg), in particular ranging from 1.3 Pa to 13 000 Pa (0.01 to 100 mmHg) and more particularly ranging from 1.3 Pa to 1300 Pa (0.01 to 10 mmHg).

Advantageously, said volatile material is lipophilic, and is thus present in the fatty phase of the emulsion. Among the odorous volatile materials that are essentially intended are essential oils and fragrancing substances, that is to say fragrancing substances other than essential oils.

Essential Oils

Essential oils differ from plant oils by the fact that they cannot be decomposed by saponification into glycerol and fatty acid soap. Moreover, they are volatile.

According to the definition given in international standard ISO 9235 and adopted by the Commission of the European Pharmacopea, an essential oil is a product generally of complex composition, obtained from a botanically defined plant raw material, either by steam entrainment, or by dry distillation, or by extraction using liquid or gaseous solvents, or via an appropriate mechanical process without heating (cold expressing). The essential oil is generally separated from the aqueous phase via a physical process which does not result in any significant change in the composition. These essential oils may also be prepared by synthesis.

The essential oil used according to the invention may be obtained from any plant material derived from the whole plant or from any part of said plant, for instance the leaves, stems, flowers, petals, seeds, fruits, buds, roots, plant branches and/or whole plants.

The essential oil used according to the invention may be prepared according to the techniques mentioned above and will preferably be obtained according to the standard technique of steam entrainment.

Among the essential oils that may be used according to the invention, mention may be made of those obtained from plants belonging to the following botanical families:

Abietaceae or Pinaceae: conifers: Amaryllidaceae: Anacardiaceae; Anonaceae; ylang ylang; Apiaceae (for example Umbelliferae): dill, *angelica*, coriander, sea fennel, carrot, parsley; Araceae; Aristolochiaceae; Asteraceae: yarrow, *artemisia*, camomile, helichrysum; Betulaceae; Brassicaceae; Burseraceae: frankincense; Caryophyllaceae; Canellaceae; Cesalpiniaceae; copaifera (copaiba balsam); Chenopodaceae; Cistaceae; rock rose; Cyperaceae; Dipterocarpaceae; Ericaceae: *gaultheria* (wintergreen); Euphorbiaceae; Fabaceae; Geraniaceae: geranium; Guttiferae; Hamamelidaceae; Hernandiaceae; Hypericaceae: St-John's wort; Iridaceae; Juglandaceae; Lamiaceae: thyme, oregano, monarda, savory, basil, marjorams, mints, patchouli, lavenders, sages, catnip, rosemary, hyssop, balm, rosemary; Lauraceae; ravensara, sweet bay, rosewood, cinnamon, *litsea*; Liliaceae: garlic; Magnoliaceae: *magnolia*; Malvaceae; Meliaceae; Monimiaceae; Moraceae: hemp, hop: Myricaceae; Myristicaceae: nutmeg; Myrtaceae: *eucalyptus*, tea tree, paperbark tree, cajuput, backhousia, clove, myrtle: Oleaceae; Piperaceae: pepper; Pittosporaceae; Poaceae: citronella grass, lemongrass, vetiver; Polygonaceae; Renonculaceae; Rosaceae: roses; Rubiaceae; Rutaceae: all *citrus* plants; Salicaceae; Santalaceae: sandalwood; Saxifragaceae; Schisandraceae; Styracaceae: benzoin; Thymelaceae: agarwood; Tiliaceae; Valerianaceae: valerian, spikenard; Verbenaceae: lantana, *verbena*; Violaceae; Zingiberaceae: galangal, turmeric, cardamom, ginger: Zygophyllaceae.

Mention may also be made of the essential oils extracted from flowers (lily, lavender, rose, jasmine, ylang ylang, neroli), from stems and leaves (patchouli, geranium, petitgrain), from fruit (coriander, aniseed, cumin, juniper), from fruit peel (bergamot, lemon, orange), from roots (*angelica*, celery, cardamom, iris, sweet flag, ginger), from wood (pinewood, sandalwood, gaiac wood, rose of cedar, camphor), from grasses and gramineae (tarragon, rosemary, basil, lemongrass, sage, thyme), from needles and branches (spruce, fir, pine, dwarf pine) and from resins and balms (*galbanum*, elemi, benzoin, myrrh, olibanum, opopanax).

The essential oil preferentially used in the compositions of the invention is chosen from essential oil of geranium, essential oil of citronella grass, essential oil of cedar, essential oil of sweet orange, essential oil of green oregano, essential oil of lemongrass, essential oil of lemon catnip, essential oil of rosemary, essential oil of mountain savory, essential oil of laserwort (Apiaceae seeds or leaf), essential oil of marjoram, essential oil of bupleurum (Asteraceae), essential oil of yarrow, essential oil of thyme, essential oil of lemon balm, essential oil of lemon, essential oil of *eucalyptus*, in particular *radiata* or *globulus*, essential oil of green or red mandarin, essential oil of clove, and essential oil of cinnamon, or mixtures thereof. Preferably, it is chosen from essential oil of geranium, essential oil of sweet orange and essential oil of green oregano.

The amount of essential oil ranges from 0.0001% to 20% by weight, preferably from 0.001% to 10% and advantageously from 0.01% to 5% by weight relative to the total weight of the composition.

Essential Oil of Geranium

According to a preferred embodiment, the composition according to the invention comprises essential oil of geranium.

Geranium is a herbaceous plant belonging to the Geraniaceae family.

Essential oil of geranium is mainly available in two varieties, namely *Pelargonium roseum* asperum CV Bourbon and *Pelargonium roseum* asperum CV North Africa (Egypt).

Their INCI name is identical, namely *Pelargonium graveolens*. Thus, it is also referred to as essential oil of *pelargonium*. In the present text, the terms "essential oil of geranium" and "essential oil of *pelargonium*" are used without any difference in meaning.

Essential oil of geranium consists essentially of a combination of three monoterpenols, namely citronellol (18% to 32%), geraniol (8% to 20%) and linalool (1.8% to 11%), and also corresponding terpenic esters.

Essential oil of geranium is prepared by conventional distillation by steam entrainment using geranium leaves and stems.

Steam entrainment corresponds to vaporization, in the presence of steam, of a sparingly water-miscible substance. The raw material is placed in contact with boiling water or steam in a stillpot. The steam entrains the essential oil vapor, which is condensed in the condenser and recovered as a liquid phase in a Florentine vase (or essence jar), where the essential oil is separated from the water by settling. The aqueous distillate that remains after the steam entrainment, once the separation of the essential oil has been performed, is known as the "aromatic water" or "hydrolate" or "distilled floral water".

An example of an essential oil of geranium according to the present invention that may be mentioned is the product sold by Elixens under the name *Pelargonium Graveolens* Flower Oil®.

Essential Oil of Citronella Grass

According to a preferred embodiment, the composition according to the invention comprises essential oil of citronella grass.

Citronella grass is a long grass originating from India and South-East Asia which may reach 1.50 m in height. It is composed of narrow, lanceolate leaves whose peduncles resemble branches. Its fragrance, similar to that of lemon, gives rise to the name of the plant. This plant from tropical regions, originating from India and Sri Lanka, also grows in Africa, South America, Central America and Madagascar. Its essential oil is obtained by distillation of the chopped leaves, which are harvested several times a year.

This distillation is performed without addition of water or steam, in a closed chamber designed so that the liquid is recovered at the bottom.

An example of an essential oil of citronella grass according to the present invention that may be mentioned is the product sold by Elixens under the name Cymbopogon Flexuosus Oil®.

Essential Oil of Sweet Orange

According to a preferred embodiment, the composition according to the invention comprises essential oil of sweet orange.

Orange is the fruit of the orange tree (*Citrus sinensis*), which belongs to the Rutaceae family. Essential oil of sweet orange is preferably obtained by expressing (pressing and scratching) orange zests. Essential oil of sweet orange has the INCI name: *Citrus Aurantium Dulcis* Peel Oil.

An essential oil of sweet orange that may be mentioned is the product *Citrus Aurantium Dulcis* Peel Oil sold by the company Elixens.

This production method generally applies only to *citrus* fruits (*Citrus* spp.) via mechanical processes at room temperature. The principle of the method is as follows: the zests are torn into pieces and the contents of the secretory sacs that have been broken are recovered by a physical process. The standard process consists in exerting an abrasive action on the entire surface of the fruit under a stream of water. After removal of the solid waste, the essential oil is separated from the aqueous phase by centrifugation. The majority of industrial installations allow simultaneous or sequential recovery of the fruit juices and of the essential oil.

Essential Oil of Green Oregano

According to a preferred embodiment, the composition according to the invention comprises essential oil of green oregano.

Essential oil of green oregano, *Origanum heracleoticum* L., is extracted from the floral aerial parts and is predominantly composed of phenols: carvacrol, thymol and monoterpenes: para-cymene and gamma-terpinene.

This essential oil is recommended in the treatment of dandruff. It is anti-infectious with a very broad spectrum of action: very powerful antibacterial, antiviral, antifungal and antiparasitic. It affords a general tonic effect and also has immunostimulatory properties, as well as appetite-stimulating and digestive properties.

An example of an essential oil of green oregano according to the present invention that may be mentioned is the product sold by Elixens under the name *Origanum Heracleoticum* Flower Oil®.

Essential Oil of Cedar

According to a preferred embodiment, the composition according to the invention comprises essential oil of cedar.

Cedar is a conifer (*Cedrus*) from the Pinaceae family. Essential oil of cedar is preferably obtained by steam entrainment, the method explained previously. Essential oil of cedar has the INCI name: *Cedrus Atlantica* Wood Oil.

An example of an essential oil of cedar according to the present invention that may be mentioned is the product sold by Elixens under the name *Cedrus Atlantica* Wood Oil®.

Essential Oil of Lemon Catnip

According to one embodiment of the invention, the composition according to the invention comprises essential oil of lemon catnip (*Nepeta cataria* L. *citriodora* BECK). Such an essential oil that is suitable for use in the invention may be obtained by extraction by steam distillation of the floral heads. In particular, an essential oil of lemon catnip mainly comprises a mixture of monoterpenols, monoterpenals and terpenes.

Essential Oil of Rosemary

According to one embodiment of the invention, the composition according to the invention comprises essential oil of rosemary.

An essential oil of rosemary (Rosmarinum *officinalis* Chemotype Cineole or Rosmarinum *officinalis* 'pyramidalis') that is suitable for use in the invention may be obtained by extraction by steam distillation of the leaves.

An essential oil of North African rosemary mainly comprises a mixture of terpenic oxides, monoterpenones, monoterpenes, monoterpenols, sesquiterpenes, terpenic esters, and also traces of verbenone, terpinolene, γ-terpinene, linalool, and para-cymene.

Essential Oil of Mountain Savory

According to one embodiment of the invention, the composition according to the invention comprises essential oil of mountain savory.

An essential oil of mountain savory (*Satureja montana* L. *Satureja montana* L. ssp montana) that is suitable for use in the invention may be obtained by extraction of the plant and of the flowers by steam distillation. An essential oil of mountain savory mainly comprises a mixture of phenols, monoterpenes, sesquiterpenes, terpenic oxides and monoterpenols.

Essential Oil of Thyme

According to one embodiment of the invention, the composition according to the invention comprises essential oil of thyme.

An essential oil of thyme (*Thymus vulgaris* CT thymol) that is suitable for use in the invention may be obtained by steam distillation of the floral heads of the plant. In particular, an essential oil of thyme mainly comprises phenols (thymol and carvacrol) and alcohols (terpinene and borneol).

Essential Oil of Lemon Balm

According to one embodiment of the invention, the composition according to the invention comprises essential oil of lemon balm.

An essential oil of lemon balm (*Melissa officinalis* L.) that is suitable for use in the invention may be obtained by extraction of the aerial parts by steam distillation. The aerial parts are preferentially harvested from June to September. In particular, an essential oil of lemon balm mainly comprises a mixture of aldehydes, sesquiterpenes, monoterpenes, terpenic esters, alcohols and nonvolatile compounds.

Essential Oil of Clove

According to one embodiment of the invention, the composition in accordance with the invention comprises essential oil of clove.

An essential oil of clove (*Eugenia caryophyllus* or *E. aromatica* Syzygium *aromaticum*) that is suitable for use in the invention may be obtained by extraction by steam distillation of the clove (floral bud). In particular, an essential oil of clove mainly comprises a mixture of phenol, sesquiterpenes and esters.

Essential Oil of Cinnamon

According to one embodiment of the invention, the composition in accordance with the invention comprises essential oil of cinnamon.

An essential oil of cinnamon (*Cinnamomum cassia*) that is suitable for use in the invention may be obtained by steam distillation of the tree bark. In particular, an essential oil of cinnamon mainly comprises an aromatic aldehyde, cinnamaldehyde, and also phenols such as chavicol and isoeugenol.

Essential Oil of Lemon

According to a preferred embodiment, the composition according to the invention comprises essential oil of lemon.

An essential oil of lemon (*Citrus limonum* L.) is preferably obtained by expressing (pressing and scratching) lemon zests.

Essential Oil of *Eucalyptus*

According to a preferred embodiment, the composition according to the invention comprises essential oil of *eucalyptus*, preferably *radiata* or *globulus*.

An essential oil of eucalyptus (*Eucalyptus radiata* LABILL) that is suitable for use in the invention may be obtained by steam distillation of the tree leaves.

Essential Oil of Green or Red Mandarin

According to a preferred embodiment, the composition according to the invention comprises essential oil of green or red mandarin.

An essential oil of green mandarin (*Citrus reticulata* blanco) is preferably obtained by expressing (pressing and scratching) mandarin zests.

Fragrancing Substances

The odorous volatile material may also be chosen from fragrancing substances, or perfumes, other than essential oils.

Perfumes are compositions especially containing the starting materials described in S. Arctander, Perfume and Flavor Chemicals (Montclair, N.J., 1969), in S. Arctander, Perfume and Flavor Materials of Natural Origin (Elizabeth, N.J., 1960) and in Flavor and Fragrance Materials-1991, Allured Publishing Co., Wheaton, III.

They may also be natural products, absolutes, resinoids, resins, concretes, and/or synthetic products (terpene or sesquiterpene hydrocarbons, alcohols, phenols, aldehydes, ketones, ethers, acids, esters, nitriles or peroxides, which may be saturated or unsaturated, and aliphatic or cyclic).

Examples of fragrancing substances are especially: geraniol, geranyl acetate, farnesol, borneol, bornyl acetate, linalool, linalyl acetate, linalyl propionate, linalyl butyrate, tetrahydrolinalool, citronellol, citronellyl acetate, citronellyl formate, citronellyl propionate, dihydromyrcenol, dihydromyrcenyl acetate, tetrahydromyrcenol, terpineol, terpinyl acetate, nopol, nopyl acetate, nerol, neryl acetate, 2-phenylethanol, 2-phenylethyl acetate, benzyl alcohol, benzyl acetate, benzyl salicylate, styrallyl acetate, benzyl benzoate, amyl salicylate, dimethylbenzylcarbinol, trichloromethylphenylcarbinyl acetate, p-tert-butylcyclohexyl acetate, isononyl acetate, vetiveryl acetate, vetiverol, α-hexylcinnamaldehyde, 2-methyl-3-(p-tert-butylphenyl)propanal, 2-methyl-3-(p-isopropylphenyl)propanal, 3-(p-tert-butylphenyl)propanal, 2,4-dimethylcyclohex-3-enylcarboxaldehyde, tricyclodecenyl acetate, tricyclodecenyl propionate, 4-(4-hydroxy-4-methylpentyl)-3-cyclohexenecarboxaldehyde, 4-(4-methyl-3-pentenyl)-3-cyclohexenecarboxaldehyde, 4-acetoxy-3-pentyltetrahydropyran, 3-carboxymethyl-2-pentylcyclopentane, 2-n-4-heptylcyclopentanone, 3-methyl-2-pentyl-2-cyclopentenone, menthone, carvone, tagetone, geranylacetone, n-decanal, n-dodecanal, 9-decen-1-ol, phenoxyethyl isobutyrate, phenylacetaldehyde dimethyl acetal, phenylacetaldehyde diethyl acetal, geranonitrile, citronellonitrile, cedryl acetate, 3-isocamphylcyclohexanol, cedryl methyl ether, isolongifolanone, aubepinonitrile, aubepine, heliotropin, coumarin, eugenol, vanillin, diphenyl ether, citral, citronellal, hydroxycitronellal, damascone, ionones, methylionones, isomethylionones, solanone, irones, cis-3-hexenol and esters thereof, musk-indans, musk-tetralins, musk-isochromans, macrocyclic ketones, musk-macrolactones, aliphatic musks, ethylene brassylate and rose essence, and mixtures thereof.

According to a preferred embodiment of the invention, a mixture of different fragrancing substances that generate in common a note that is pleasant to the user is used.

The fragrancing substances will preferably be chosen such that they produce notes (head, heart and base) in the following families: *citrus*, aromatic, floral, spicy, woody, gourmand, chypre, fougere, leathery, musk.

The amount of fragrancing substance(s) is generally at least 0.01% by weight, preferably not more than 30% by weight, in particular from 0.1% to 10% by weight, preferably from 0.3% to 10%, and especially from 0.1% to 5% or from 0.3% to 5% relative to the total weight of the composition.

Aqueous Phase

The water may be present in a total content ranging from 30% to 90%, preferably 40% to 85% by weight, relative to the total weight of the composition.

Preferably, the composition according to the invention comprises at least 30% by weight of water, preferably at least 40% by weight and preferably at least 50% by weight, relative to the total weight of the composition.

The composition in accordance with the invention may comprise, besides water, at least one water-soluble solvent.

The aqueous phase constitutes the continuous phase of the composition.

The term "composition with an aqueous continuous phase" means that the composition has a conductivity, measured at 25° C., of greater than or equal to 23 uS/cm (microSiemens/cm), the conductivity being measured, for example, using an MPC227 conductimeter from Mettler Toledo and an Inlab730 conductivity measuring cell. The measuring cell is immersed in the composition so as to remove the air bubbles that might be formed between the two electrodes of the cell. The conductivity reading is taken once the conductimeter value has stabilized. A mean is determined on at least three successive measurements.

The water used in the composition of the invention may be demineralized pure water, but also mineral water and/or spring water and/or seawater, i.e. the water of the composition may be partially or totally constituted of water chosen from mineral waters, spring waters, seawaters and mixtures thereof. In general, a mineral water is fit for consumption, which is not always the case for a spring water. Each of these waters contains, inter alia, dissolved minerals and/or trace elements. These waters are known to be employed for specific treatment purposes according to the particular trace elements and minerals that they contain, such as moisturization and desensitization of the skin or the treatment of certain dermatoses. The terms "mineral water" and "spring water" will denote not only natural mineral or spring waters but also natural mineral or spring waters enriched in additional mineral constituents and/or trace elements, and also aqueous mineral solutions and/or solutions containing trace elements prepared from purified water (demineralized or distilled water). A natural spring water or mineral water used according to the invention may be chosen, for example, from Vittel water, Vichy basin water, Uriage water, Roche Posay water, Bourboule water, Enghien-les-Bains water, Saint Gervais-les-Bains water, Neris-les-Bains water, Allevar-les-Bains water, Digne water, Maizières water, Neyrac-les-Bains water, Lons-le-saunier water, Eaux Bonnes water, Rochefort water, Saint Christau water, Fumades water, Tercis-les-bains water and Avene water.

The water used in the composition of the invention may also be a water prepared from a plant, such as a "plant water" when it is obtained from a whole plant or from a part thereof, or a "floral water" when said water is obtained from flowers. Such waters obtained from a plant (or any botanically defined plant raw material), in particular a whole plant and/or a part of a plant, are also referred to as "hydrolate".

The term "hydrolate" means an aqueous distillate obtained from a plant raw material by steam entrainment. Steam entrainment corresponds to the vaporization, in the presence of steam, of a sparingly water-miscible substance.

The hydrolate according to the invention may be an aqueous distillate, obtained from a whole plant and/or a part of this plant, which remains after the steam entrainment, once the separation of the essential oil has been performed. The raw material may be placed in contact with boiling water or steam in a stillpot. The steam entrains the essential oil vapor, which is condensed in the condenser and recovered as a liquid phase in a Florentine vase (or essence jar), where the essential oil is separated from the water by settling. The "hydrolate" is thus the aqueous distillate that remains after the steam entrainment, once the separation of the essential oil has been performed. A hydrolate according to the invention may also be referred to as "aromatic water".

The hydrolate may be obtained from a whole plant, preferably a plant, a shrub or a flower, or from a part of this plant chosen from flowers, leaves, stems, seeds, fruits, roots, petals and buds, which can be in various states of dryness (dry, withered, fresh form), and mixtures thereof.

In particular in the context of the present invention, the hydrolate is a hydrolate of a plant and/or of a plant part chosen from the Rosaceae family, preferably of the genus *Rosa*, the Asteraceae family, preferably of the genus *Centaurea* and/or of the genus *Chamaemelum*, the Lamiaceae family, preferably of the genus *Lavandula*, the Rutaceae family, preferably of the genus *Citrus*, the Lamiaceae family, preferably of the genus *Melissa* and/or of the genus *Mentha*, the Verbenaceae family, preferably of the genus *Aloysia*, and mixtures thereof.

More particularly in the context of the present invention, the hydrolate is a hydrolate of a plant and/or of a part of a plant chosen from *Rosa damascena, Centaurea cyanus, Anthemis nobilis* or *Chamaemelum nobile, Lavandula angustifolia, Citrus aurantium amara, Melissa officinalis, Mentha piperita* and Lippia *citriodora*, and mixtures thereof.

In the present invention, the term "water-soluble solvent" denotes a compound that is liquid at room temperature and water-miscible (miscibility with water of greater than 50% by weight at 25° C. and atmospheric pressure).

The water-soluble solvents that may be used in the compositions according to the invention may also be volatile.

Among the water-soluble solvents that may be used in the compositions in accordance with the invention, mention may be made in particular of lower monoalcohols containing from 1 to 5 carbon atoms, such as ethanol and isopropanol.

In the present invention, the term "polyol" means glycols containing from 2 to 8 carbon atoms, such as ethylene glycol, propylene glycol, 1,3-butylene glycol and dipropylene glycol, C3 and C4 ketones and C2-C4 aldehydes, or polyols, for instance glycerol.

As already mentioned, the composition according to the invention comprises less than 3%, preferably less than 1% by weight of glycol(s) or of polyol(s) relative to the total weight of the composition. Advantageously, the composition according to the invention is free of glycol(s) and/or polyol(s).

Advantageously, the glycol(s)/spiculisporic acid or polyol(s)/spiculisporic acid ratio is less than 1, preferably less than 0.2.

The aqueous phase (water and optionally the water-miscible solvent) may be present in the composition in a content ranging from 0.1% to 99.9% by weight and preferably ranging from 40% to 95% by weight relative to the total weight of the composition.

Thickener

A composition according to the invention may comprise at least one hydrophilic gelling agent as thickener.

Preferably, the hydrophilic gelling agents are polymeric and they are advantageously natural or of natural origin.

For the purposes of the invention, the term "of natural origin" is intended to denote polymeric gelling agents obtained by modification of natural polymeric gelling agents.

These gelling agents may be particulate or non-particulate.

More specifically, these gelling agents fall within the category of polysaccharides.

Advantageously, the polysaccharides may be chosen from carrageenans, in particular kappa-carrageenan, gellan gum, agar-agar, xanthan gum, alginate-based compounds, in particular sodium alginate, scleroglucan gum, guar gum, inulin and pullulan, and mixtures thereof.

Preferably, the hydrophilic gelling agent is xanthan gum.

Depending on the intended application, a composition according to the invention may also comprise one or more fillers conventionally used in compositions, especially care and/or makeup compositions, dyestuffs, especially pigments, nacres and particles with a metallic tint.

One advantage of the present invention is that it allows homogeneous dispersion of these fillers, nacres and pigments in the composition.

Needless to say, a person skilled in the art will choose these additives so that they are compatible with the other components of the composition.

Filler

A composition according to the invention may also comprise one or more fillers conventionally used in compositions, especially care and/or makeup compositions, and other than pigments, nacres and particles with a metallic tint.

These fillers are colorless or white solid particles of any form, which are in a form that is insoluble and dispersed in the medium of the composition.

These fillers, of mineral or organic, natural or synthetic nature, give the composition containing them softness, a matt effect and uniformity of the makeup result. In addition, these fillers advantageously make it possible to combat various attacking factors such as sebum or sweat.

As illustrations of these fillers, mention may be made of talc, mica, silica, kaolin, poly-β-alanine powder and polyethylene powder, powders of tetrafluoroethylene polymers (Teflon®), lauroyllysine, starch, boron nitride, hollow polymer microspheres such as those of polyvinylidene chloride/acrylonitrile, for instance Expancel® (Nobel Industrie), acrylic acid copolymer microspheres, silicone resin microbeads (for example Tospearls® from Toshiba), polyorganosiloxane elastomer particles, precipitated calcium carbonate, magnesium carbonate, magnesium hydrogen carbonate, hydroxyapatite, barium sulfate, polyurethane powders, composite fillers, hollow silica microspheres, and glass or ceramic microcapsules. Use may also be made of particles that are in the form of hollow sphere portions, as described in patent applications JP-2003 128 788 and JP-2000 191 789.

In particular, such fillers may be present in a composition according to the invention in a content of between 0.01% and 25% by weight, in particular between 0.1% and 20% by weight and in particular between 1% and 10% by weight relative to the total weight of the composition.

Nacres

The composition according to the invention may also comprise at least one nacre.

The term "nacres" should be understood as meaning iridescent or non-iridescent colored particles of any shape, especially produced by certain molluscs in their shell or alternatively synthesized, which have a color effect via optical interference.

A composition according to the invention may comprise from 0% to 15% by weight of nacres relative to the total weight of said composition.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles, at the surface of which are superposed at least two successive layers of metal oxides and/or of organic dyestuffs.

Examples of nacres that may also be mentioned include natural mica covered with titanium oxide, with iron oxide, with natural pigment or with bismuth oxychloride.

Among the nacres available on the market, mention may be made of the nacres Timica, Flamenco and Duochrome (based on mica) sold by the company Engelhard, the Timiron nacres sold by the company Merck, the Prestige mica-based nacres, sold by the company Eckart, and the Sunshine synthetic mica-based nacres, sold by the company Sun Chemical.

The nacres may more particularly have a yellow, pink, red, bronze, orange, brown, gold and/or coppery color or tint.

Advantageously, the nacres in accordance with the invention are micas covered with titanium dioxide or with iron oxide, and also bismuth oxychloride.

Pigments

As stated previously, a composition may also contain pigments.

These pigments may be mineral pigments especially as defined previously.

These pigments may also be organic pigments.

The term "organic pigment" means any pigment that satisfies the definition in Ullmann's Encyclopedia in the chapter on organic pigments. The organic pigment may in particular be chosen from nitroso, nitro, azo, xanthene, quinoline, anthraquinone, phthalocyanine, metal complex type, isoindolinone, isoindoline, quinacridone, perinone, perylene, diketopyrrolopyrrole, thioindigo, dioxazine, triphenylmethane and quinophthalone compounds.

The organic pigment(s) may be chosen, for example, from carmine, carbon black, aniline black, melanin, azo yellow, quinacridone, phthalocyanin blue, sorghum red, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and the pigments obtained by oxidative polymerization of indolic or phenolic derivatives as described in patent FR 2 679 771.

These pigments may also be in the form of composite pigments as described in patent EP 1 184 426. These composite pigments may in particular be composed of particles comprising a mineral core at least partially coated with an organic pigment and at least one binder for fixing the organic pigments to the core.

The pigment may also be a lake. The term "lake" means insolubilized dyes adsorbed onto insoluble particles, the assembly thus obtained remaining insoluble during use.

The mineral substrates onto which the dyes are adsorbed are, for example, alumina, silica, calcium sodium borosilicate or calcium aluminum borosilicate and aluminum.

Among the organic dyes, mention may be made of cochineal carmine. Mention may also be made of the products known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 10 (CI 77 002), D&C Green 3 (CI 42 053), D&C Blue 1 (CI 42 090).

An example of a lake that may be mentioned is the product known under the name D&C Red 7 (CI 15 850:1).

In a preferred embodiment, the composition according to the invention also comprises at least one UV-screening agent and/or one additive chosen from fillers, dyestuffs such as pigments, nacres or particles with a metallic tint, moisturizers, antiwrinkle or antiaging agents, desquamating agents, antioxidants, active agents for stimulating the synthesis of dermal and/or epidermal macromolecules, dermo-decontracting agents, depigmenting agents and deodorants, and mixtures thereof.

Advantageously, a composition according to the invention may comprise at least one UV-screening agent.

UV-Screening Agent

This screening agent is chosen from UV-A- and/or UV-B-screening agents.

Even more particularly, said UV-screening agent is chosen from water-soluble organic UV-screening agents, liposoluble organic screening agents, and mixtures thereof, and more particularly liposoluble organic UV-screening agents.

By way of nonlimiting illustration of UV-screening agents, mention may be made of anthranilates, in particular menthyl anthranilate; benzophenones, in particular benzophenone-1, benzophenone-3, benzophenone-5, benzophenone-6, benzophenone-8, benzophenone-9 and benzophenone-12, and preferentially benzophenone-2 (Oxybenzone), or benzophenone-4 (Uvinul MS40R available from BASF); benzylidenecamphors, in particular 3-benzylidenecamphor, benzylidenecamphorsulfonic acid, camphor benzalkonium methosulfate, polyacrylamidomethylbenzylidenecamphor, terephthalylidenedicamphorsulfonic acid, and preferentially 4-methylbenzylidenecamphor (Eusolex 6300® available from Merck); benzimidazoles, in particular benzimidazilate (Neo Heliopan APR available from Haarmann and Reimer), or phenylbenzimidazolesulfonic acid (Eusolex 232®) available from Merck): benzotriazoles, in particular drometrizole trisiloxane, or methylenebisbenzotriazolyltetramethylbutylphenol (Tinosorb M® available from Ciba); cinnamates, in particular cinoxate, DEA methoxycinnamate, diisopropyl methylcinnamate, glyceryl ethylhexanoate dimethoxycinnamate, isopropyl methoxycinnamate, isoamyl cinnamate, preferentially Etocrylene (Uvinul N35® available from BASF), octyl methoxycinnamate (Parsol MCX® available from Hoffman LaRoche) or Octocrylene (Uvinul 539® available from BASF); dibenzoylmethanes, in particular butyl methoxydibenzoylmethane (Parsol 1789®); imidazolines, in particular ethylhexyl dimethoxybenzylidene dioxoimidazoline; PABA, in particular ethyldihydroxypropyl PABA, ethylhexyldimethyl PABA, glyceryl PABA, PABA, PEG-25 PABA, and preferentially diethylhexylbutamidotriazone (Uvasorb HEBR) available from 3V Sigma), ethylhexyltriazone (Uvinul T150R available from BASF), or ethyl PABA (benzocaine); Mexoryl®; salicylates, in particular dipropylene glycol salicylate, ethylhexyl salicylate, homosalate, or TEA salicylate; triazines, in particular anisotriazine (Tinosorb SR available from Ciba); drometrizole trisiloxane, zinc oxide, titanium dioxide, and coated or uncoated zinc, iron, zirconium or cerium oxide.

In a preferred embodiment, the presence of spiculisporic acid in the compositions according to the invention comprising sunscreens results in a surprising increase in the SPF compared with equivalent compositions not comprising spiculisporic acid.

Additional Dispersant

Advantageously, a composition according to the invention may also comprise an additional dispersant.

Such a dispersant may be a surfactant, an oligomer, a polymer or a mixture of several thereof.

When the composition according to the invention comprises an additional surfactant, said surfactant is preferably present in a content of less than 5%, preferably less than 3%, preferably less than 2%, preferably less than 1%, preferably less than 0.5% by weight relative to the total weight of the composition. In one preferred embodiment, the composition according to the invention does not contain any additional surfactant.

In another preferred embodiment, the composition according to the invention does not comprise any sulfate-based and/or sulfonate-based surfactant, for instance those described in patent application WO 2015/067785.

According to a particular embodiment, a dispersant in accordance with the invention is a surfactant.

Active Agent

According to a particular embodiment, the composition according to the invention may also comprise at least one additional active agent chosen from moisturizers, antiwrinkle or antiaging agents, desquamating agents, antioxidants, active agents for stimulating the synthesis of dermal and/or epidermal macromolecules, dermo-decontracting agents, depigmenting agents, deodorants and fragrances, and mixtures thereof.

These additional active agents may be present in the composition according to the invention in a content ranging from 0.001% to 30% by weight, preferably from 0.01% to 20% by weight and more preferentially from 0.1% to 15% by weight, relative to the total weight of the composition comprising them.

Antiwrinkle or Antiaging Agents

As representative antiwrinkle or antiaging agents that may be used in the present invention, mention may be made more particularly of adenosine, retinol and derivatives thereof, ascorbic acid and derivatives thereof, such as magnesium ascorbyl phosphate and ascorbyl glucoside; tocopherol and derivatives thereof, such as tocopheryl acetate; nicotinic acid and precursors thereof, such as nicotinamide; ubiquinone; glutathione and precursors thereof, such as L-2-oxothiazolidine-4-carboxylic acid; C-glycoside compounds and derivatives thereof, as especially described below: plant extracts and especially extracts of sea fennel and of olive leaf, and also plant proteins and hydrolyzates thereof, such as rice or soybean protein hydrolyzates; or extracts of *Vigna aconitifolia* seeds such as those sold by the company Cognis under the references Vitoptine LS9529 and Vit-a-Like LS9737; algal extracts and in particular *laminaria* extracts; bacterial extracts; sapogenins, such as diosgenin and extracts of *Dioscorea* plants, in particular of wild yam, containing same; α-hydroxy acids; β-hydroxy acids such as salicylic acid and 5-n-octanoylsalicylic acid; oligopeptides and pseudodipeptides and acyl derivatives thereof, in particular {2-[acetyl-(3-trifluoromethylphenyl)amino]-3-methylbutyrylamino}acetic acid and the lipopeptides sold by the company Sederma under the trade names Matrixyl 500 and Matrixyl 3000; lycopene; manganese and magnesium salts, in particular the gluconates; and mixtures thereof.

Humectants or Moisturizers

Humectants or moisturizers that may in particular be mentioned include an extract of Aloe vera, urea and derivatives thereof, in particular Hydrovance® sold by National Starch, monosaccharides such as mannose, hyaluronic acid, AHAs, BHAs, acrylic acid homopolymers such as Lipidure-HM® from NOF Corporation, β-glucan and in particular sodium carboxymethyl β-glucan from Mibelle-AG-Biochemistry; a polyoxybutylene polyoxyethylene polyoxypropylene glycerol, for instance Wilbride S-753LR from NOF Corporation, a musk rose oil sold by Nestle; collagen and chondroitin sulfate spheres of marine origin (Atelocollagen) sold by the company Engelhard Lyon under the name Sphères de Comblement Marines; hyaluronic acid spheres such as those sold by the company Engelhard Lyon.

Additional Desquamating Agents

Desquamating agents that may be mentioned include β-hydroxy acids, in particular salicylic acid and derivatives thereof other than 5-n-octanoylsalicylic acid; urea; glycolic acid, citric acid, lactic acid, tartaric acid, malic acid or mandelic acid; 4-(2-hydroxyethyl)piperazine-1-propanesulfonic acid (HEPES); extract of Saphora *japonica*: honey; N-acetylglucosamine; sodium methyl glycine diacetate, α-hydroxy acids (AHA) and β-hydroxy acids (BHA), and mixtures thereof.

Antioxidants

Antioxidants that may be mentioned more particularly include tocopherol and esters thereof, in particular tocopheryl acetate; EDTA, ascorbic acid and derivatives thereof, in particular magnesium ascorbyl phosphate and ascorbyl glucoside; chelating agents, such as BHT, BHA and N,N'-bis (3,4,5-trimethoxy benzyl)ethylenediamine and salts thereof, and mixtures thereof.

Dermo-Decontracting or Dermo-Relaxing Agents

Dermo-decontracting or dermo-relaxing agents that may be mentioned most particularly include manganese gluconate, wild yam, sea fennel, glycine and alverine.

Active Agents for Stimulating the Synthesis of Dermal and/or Epidermal Macromolecules and/or for Preventing their Degradation As active agents for stimulating the synthesis of dermal and/or epidermal macromolecules and/or for preventing their degradation, mention may be made of: peptides extracted from plants, such as the soybean hydrolyzate sold by the company BASF Beauty Care Solutions under the trade name Phytokine®, the malt extract as sold under the trade name Collalift® by the company BASF BCS; rice peptides such as Nutripeptide® from Silab, or alternatively a rice peptide extract such as Colhibin® Pentapharm DSM, methylsilanol mannuronate such as Algisium C® sold by Exsymol; an extract of *Vaccinium myrtillus* such as the products described in patent application FR-A-2 814 950; the lupin extract sold by the company Silab under the trade name Structurine®, and mixtures thereof, and *verbena* hydrolate.

Depigmenting Agents

As depigmenting agents, mention may be made of ceramides, vitamin C and derivatives thereof and in particular vitamin CG, CP and 3-O ethyl vitamin C, alpha and beta arbutin, ferulic acid, kojic acid, resorcinol and derivatives thereof, calcium D-pantheteine sulfonate, lipoic acid, ellagic acid, vitamin B3, phenylethyl resorcinol such as Symwhite 377R from the company Symrise, a kiwi fruit (*Actinidia chinensis*) juice sold by Gattefosse, and an extract of *Paeonia suffruticosa* root, such as the product sold by the company Ichimaru Pharcos under the name Botanpi Liquid B®, an extract of brown sugar (*Saccharum officinarum*), such as the extract of molasses sold by the company Taiyo Kagaku under the name Molasses Liquid, and a mixture of undecylenic acid and undecylenoyl phenylalanine, such as Sepiwhite MSHR from SEPPIC.

Deodorant Agents

As deodorant agents in accordance with the invention, mention may be made of essential oils, bacteriostatic agents or bactericidal agents that act on underarm odor microorganisms, such as 2,4,4'-trichloro-2'-hydroxydiphenyl ether (® Triclosan), 2,4-dichloro-2'-hydroxydiphenyl ether, 3',4', 5'-trichlorosalicylanilide, 1-(3',4'-dichlorophenyl)-3-(4'-chlorophenyl)urea (® Triclocarban) or 3,7,11-trimethyldodeca-2,5,10-trienol (® Farnesol).

Deodorant agents in accordance with the invention may also be chosen from quaternary ammonium salts such as cetyltrimethylammonium salts, cetylpyridinium salts, DPTA (1,3-diaminopropanetetraacetic acid), 1,2-decanediol (Symclariol from the company Symrise), glycerol derivatives, for instance caprylic/capric glycerides (Capmul MCM from Abitec), glyceryl caprylate or caprate (Dermosoft GMCY and Dermosoft GMC, respectively from Straetmans), Polyglyceryl-2 caprate (Dermosoft DGMC from Straetmans), and biguanide derivatives, for instance polyhexamethylene biguanide salts, chlorhexidine and salts thereof, and 4-phenyl-4,4-dimethyl-2-butanol (Symdeo MPP from Symrise).

Mention may also be made, as deodorant agents, of zinc salts, for instance zinc salicylate, zinc gluconate, zinc pidolate; zinc sulfate, zinc chloride, zinc lactate, zinc phenolsulfonate, or salicylic acid and derivatives thereof such as 5-n-octanoylsalicylic acid.

In addition, deodorant agents according to the invention may be chosen from odor absorbers such as zinc ricinoleates, sodium bicarbonate; metallic or nonmetallic zeolites, and cyclodextrins.

They may also be a chelating agent such as Dissolvine GL-47-S from AkzoNobel, EDTA; DPTA.

It may also be an enzyme inhibitor such as triethyl citrate.

In the event of incompatibility or to stabilize them, some of the agents mentioned above may be incorporated into spherules, in particular ionic or nonionic vesicles, and/or particles (capsules and/or spheres).

Needless to say, the deodorant agents that may be present in a composition in accordance with the invention must not impair the advantageous properties of the composition indicated previously.

The composition according to the invention may be in the form of a face and/or body care or makeup product, and may be conditioned, for example, in the form of cream in a jar or of fluid in a tube or in a pump-action bottle.

It is a matter of routine operation for those skilled in the art to adjust the nature and the amount of the additives present in the compositions in accordance with the invention such that the desired cosmetic properties thereof are not thereby affected.

According to another embodiment, a composition of the invention may advantageously be in the form of a makeup base composition.

According to another embodiment, a composition of the invention may advantageously be in the form of a foundation.

Such compositions are especially prepared according to the general knowledge of those skilled in the art.

Throughout the description, including the claims, the expression "comprising a" should be understood as being synonymous with "comprising at least one", unless otherwise specified.

The expressions "between . . . and . . . " and "ranging from . . . to . . . " should be understood as being inclusive of the limits, unless otherwise specified.

The invention is illustrated in greater detail by the examples presented below. Unless otherwise indicated, the amounts shown are expressed as weight percentages.

EXAMPLES

In the tables that follow, the amount of each compound is given as percentage by weight of active material relative to the total weight of the composition.

Example 1

Preparation of the Compositions

The compositions are prepared in a Rayneri mixer according to the following protocol:

- the water is weighed out in the preparation beaker,
- the spiculisporic acid is introduced with mechanical stirring: since it is water-insoluble, it remains in powder form,
- the base, especially arginine, is added with mechanical stirring, the powder mixture gradually dissolves, and the solution becomes completely translucent after 5 minutes of stirring,
- the oil(s) and the UV-screening agent are introduced, with continued stirring, and stirring is maintained for 10 minutes at 700-1000 rpm depending on the viscosity of the medium,
- the preserving agent is added, along with water to reach the target concentration.

Preparation of the Films

The films are prepared using a film spreader, which is in the form of a mechanical arm which sweeps a flat surface at a controlled speed.

The thickness of the films is controlled by means of test pieces with precise slit thicknesses. The film is then left in the open air in order to dry and the behavior on drying is observed. The behavior on drying reflects the way in which the surfactant structures the fatty phase on drying and also the resistance of the film obtained to ambient moisture.

TABLE 1

| Series 1 - Emulsions comprising a mono-arginine salt of spiculisporic acid | | | | | | |
|---|---|---|---|---|---|---|
| | | Ex. 1 in accordance | Ex. A comparative | Ex. B comparative | Ex. 2 in accordance | Ex. C comparative |
| A | Spiculisporic acid | 5 | 5 | 0 | 1 | 5 |
| | Arginine | 2.9 | 2.9 | 0 | 0.6 | 0 |

TABLE 1-continued

Series 1 - Emulsions comprising a mono-arginine salt of spiculisporic acid

|   |   | Ex. 1 in accordance | Ex. A comparative | Ex. B comparative | Ex. 2 in accordance | Ex. C comparative |
|---|---|---|---|---|---|---|
|   | Water | 50 | 50 | 50 | 50 | 50 |
|   | Potassium hydroxide | 0 | 0 | 0 | 0 | 1.9 |
| B | Jojoba oil | 5 | 5 | 5 | 5 | 5 |
|   | Octyldodecanol | 10 | 10 | 10 | 10 | 10 |
|   | Stabilized dioctyl oxide | 5 | 5 | 5 | 5 | 5 |
|   | Ethylhexyl methoxycinnamate, sold under the name Parsol MCX by DSM Nutritional Products | 1 | 1 | 1 | 1 | 1 |
| C | Glycerol | 0 | 5 | 0 | 0 | 0 |
| D | Xanthan | 0.4 | 0.4 | 1 | 0.4 | 0.4 |
| E | Preserving agent | 0.5 | 0.5 | 0.5 | 0.5 | 0.5 |
|   | Water | qs 100 | qs 100 | qs 100 | qs 100 | qs 100 |

Results

Examples in Accordance

Example 1 comprising 5% of mono-arginine salt of spiculisporic acid leads, after drying, to the formation of a stable homogeneous film. The film remains stable after storage for two weeks in the open air and at room temperature. Specifically, no coalescence of the emulsion, nor any phase separation, is observed. The film obtained is dry and "rigid" in the sense that it can be handled.

Example 2 comprising 1% of mono-arginine salt of spiculisporic acid leads, after drying, to the formation of a stable homogeneous film. The film is stable after storage for two weeks in the open air and at room temperature. Specifically, no coalescence of the emulsion, nor any phase separation, is observed.

Comparative Examples

Example A comprising 5% of mono-arginine salt of spiculisporic acid and 5% of glycerol leads, after drying, to the formation of a non-homogeneous film which contains holes. The film stability is poor. The film rapidly becomes greasy and tacky and it cannot be handled.

After one hour, clear phase separation of the emulsion is observed.

The same results were observed on replacing the 5% of glycerol with 5% of propanediol.

The emulsion of Example B, without spiculisporic acid, comprising 1% of xanthan is not stable; phase separation is rapidly observed after preparation. Moreover, this emulsion does not produce a stable homogeneous film. This example shows that xanthan alone does not make it possible to obtain a composition with film-forming properties.

The emulsion of Example C comprising 5% of monopotassium salt of spiculisporic acid is stable after the preparation but, after 10 hours, the emulsion exhibits crystals. The film obtained after drying rapidly shows phase separation.

TABLE 2

Series 2 - Emulsions comprising an arginine salt of spiculisporic acid - variation of the fatty phase

|   |   | Ex. 3 in accordance | Ex. 4 in accordance | Ex. 5 in accordance | Ex. 6 in accordance |
|---|---|---|---|---|---|
| A | Spiculisporic acid | 5 | 5 | 5 | 5 |
|   | Arginine | 2.9 | 2.9 | 2.9 | 2.9 |
|   | Water | 50 | 50 | 50 | 50 |
| B | Octyldodecanol | 20 | 0 | 0 | 0 |
|   | Stabilized dioctyl oxide | 0 | 20 | 0 | 0 |
|   | Squalane | 0 | 0 | 20 | 0 |
|   | Olive oil | 0 | 0 | 0 | 20 |
|   | Ethylhexyl methoxycinnamate, sold under the name Parsol MCX by DSM Nutritional Products | 1 | 1 | 1 | 1 |
| C | Xanthan | 0.4 | 0.4 | 0.4 | 0.4 |
| E | Preserving agent | 0.5 | 0.5 | 0.5 | 0.5 |
|   | Water | qs 100 | qs 100 | qs 100 | qs 100 |

Results

Emulsions were prepared using oils of very different polarity: from the least polar (squalane) to the most polar (olive oil). In all cases, stable emulsions resulting in films of good quality were obtained.

TABLE 3

Series 3 - Emulsions comprising an arginine salt of spiculisporic acid - variation of the amount of fatty phase

|   |   | Ex. 1 in accordance | Ex. 7 in accordance | Ex. 8 in accordance |
|---|---|---|---|---|
| A | Spiculisporic acid | 5 | 5 | 5 |
|   | Arginine | 2.9 | 2.9 | 2.9 |
|   | Water | 50 | 30 | 20 |
| B | Jojoba oil | 5 | 10 | 15 |
|   | Octyldodecanol | 10 | 20 | 30 |

TABLE 3-continued

Series 3 - Emulsions comprising an arginine salt of spiculisporic acid - variation of the amount of fatty phase

|   |   | Ex. 1 in accordance | Ex. 7 in accordance | Ex. 8 in accordance |
|---|---|---|---|---|
|   | Stabilized dioctyl oxide | 5 | 10 | 15 |
|   | Ethylhexyl methoxycinnamate, sold under the name Parsol MCX by DSM Nutritional Products | 1 | 1 | 1 |
| D | Xanthan | 0.4 | 0.4 | 1 |
| E | Preserving agent | 0.5 | 0.5 | 0.5 |
|   | Water | qs 100 | qs 100 | qs 100 |

Results

All the O'W emulsions obtained, even with a high fatty phase content, are stable and lead to films of good quality: these films are homogeneous, show good persistence, and have a dry, non-greasy feel.

TABLE 4

Series 4 - Emulsions comprising film-forming polymers or a synthetic surfactant

|   |   | Ex. D comparative | Ex. E comparative | Ex. F comparative |
|---|---|---|---|---|
| A | Sodium Lauroyl Glutamate (SLG) | 5 | 0 | 0 |
|   | Water | 50 | 30 | 20 |
| B | Jojoba oil | 5 | 5 | 5 |
|   | Octyldodecanol | 10 | 10 | 10 |
|   | Stabilized dioctyl oxide | 5 | 5 | 5 |
|   | Ethylhexyl methoxycinnamate, sold under the name Parsol MCX by DSM Nutritional Products | 1 | 1 | 1 |
| D | Xanthan | 0.4 | 0 | 0 |
|   | Alginate | 0 | 2 | 0 |
|   | Acrylic acid/stearyl methacrylate copolymer | 0 | 0 | 1.4 |
|   | 2-Amino-2-methyl-1-propanol | 0 | 0 | 0.8 |
| E | Preserving agent | 0.5 | 0.5 | 0.5 |
|   | Water | qs 100 | qs 100 | qs 100 |

Results

In the composition of Comparative Example D, SLG (synthetic surfactant) and xanthan are used in order to stabilize the emulsion formed and to be able to prepare a film. The film thus obtained spreads well but is not stable after drying, since coalescence is observed.

In each of the compositions of Comparative Examples E and F, a film-forming polymer is used; these polymers do not make it possible to produce stable emulsions and the films obtained are non-homogeneous. The polymers tested do not make it possible to stabilize a fatty film.

Series 4-Characterization of the Film Formed with the Spiculisporic Acid Emulsions According to the Invention The films formed after drying the emulsions according to the invention comprising spiculisporic acid were characterized with a surface analyzer by measuring the contact angle with a drop of water.

The angle measurement was performed with an MSA surface analyzer (Krüss). The formulations were applied on a SkinFX support (silicone-based support 80 mm in diameter, covered with a polyurethane film) and left to dry for a time of 20 minutes. A drop of water is then placed on the surface of the film and viewed with a camera.

The contact angle is measured and reported in a table.

Various emulsions are evaluated, by varying the spiculisporic acid concentration, the polarity of the oil, the nature of the oil mixtures and the oil content. The emulsions tested are listed in the table below.

| Formulation | Emulsion G (In accordance) | Emulsion H (In accordance) | Emulsion I (In accordance) | Emulsion J (In accordance) | Emulsion K (In accordance) |
|---|---|---|---|---|---|
| Spiculisporic acid | 5 | 1 | 1 | 1 | 1 |
| Arginine | 1.1 | 1.1 | 1.1 | 1.1 | 1.1 |
| Octyldodecanol | 20 | 20 | 40 | 60 | 0 |
| Coconut oil | 0 | 0 | 0 | 0 | 60 |
| Xanthan | 0.4 | 0.4 | 0.4 | 0.4 | 0.4 |
| Ethylhexyl methoxycinnamate, sold under the name Parsol MCX by DSM Nutritional Products | 1 | 1 | 1 | 1 | 1 |
| Water | qs 100 | qs 100 | qs 100 | qs 100 | qs 100 |
| CA(M) [°] | 24.49 | 21.19 | 17.17 | 17.47 | 15.37 |
| ± | 13.98 | 1.09 | 4.29 | 3.62 | 2.59 |

The results obtained show that, irrespective of the nature of the oily phase, its concentration or the spiculisporic acid concentration, the contact angle of the film formed with the water drop does not change significantly (the measurement of the angle taken on the SkinFX skin alone, i.e. skin not covered with a film according to the present invention, is 123.26 CA(M) [°]±2.42. The film formed with each of the emulsions G to K is of hydrophilic nature. The formation of such hydrophilic films is of great interest for implementation in varied cosmetic applications, such as anti-pollution, moisturization, makeup or haircare.

Example 2: Compositions Comprising Essential Oils

Preparation of the compositions
The following compositions are prepared as described in Example 1 above.

|  |  | Comparative Ex. 1 | Comparative Ex. 2 | Ex. 3 in accordance |
|---|---|---|---|---|
| Essential oil of green oregano | EO of bio green oregano SICA (ELIXENC)° | 1 | 1 | 1 |
| Xanthan | Rhodicare CFT (Solvay) | 0 | 0.50 | 0.50 |
| Acrylates/ C10-30 alkyl acrylate crosspolymer | Pemulen TR-1 Polymer (Lubrizol) | 1.40 | 0 | 0 |
| Aminomethyl-propanol | AMP Ultra PC 1000, neutralizing amine (Angus-Dow Chemicals) | 0.8 | 0 | 0 |
| Squalane | Olive Squalane (Deoleo) | 10 | 10 | 10 |
| Spiculisporic acid | Iwata Chemicals | 0 | 0 | 5 |
| Cocoyl glucoside | Plantacare 818 UP (BASF) | 0 | 5 | 0 |
| Arginine | Ajinomoto | 0 | 0 | 3 |
| Water |  | qs 100 | qs 100 | qs 100 |

Preparation of the Films and Experimental Evaluation Method

The experimental evaluation method is a thin-film evaporation test.

The protocol is as follows: the emulsion is applied to a hydrophobic filter using a film spreader in the form of a mechanical arm which sweeps over a flat surface at a controlled speed to form a film with a controlled thickness of 50 microns. The film is then left to evaporate under a controlled stream of air (Sorbonne). Samples were taken at various times to assay the amount of essential oil remaining on the film via an extraction process using solvents and detection by UV-visible spectroscopy. On account of the complexity of the composition of the essential oil of green oregano, only the major component, carvacrol (about 50%), was assayed.

| | Proportion of essential oil of green oregano remaining in the film (%) Mean of two tests N = 2 | |
|---|---|---|
| | t = 10 minutes | t = 3 hours |
| Composition Ex. 1 (comparative) | 59.82% | 23.04% |
| Composition Ex. 2 (comparative) | 74.84% | 19.24% |
| Composition Ex. 3 (invention) | 85.38% | 43.01% |

After drying for 3 hours, the remaining amount of essential oil of green oregano is twice as large when the film formed was prepared with spiculisporic acid.

The results showed that spiculisporic acid increases by a factor of two the remaining amount of essential oil of green oregano after a drying time of 3 hours, when compared with cocoyl glucoside (nonionic surfactant) or with the acrylates/ C10-30 alkyl acrylate crosslinked polymer Pemulen TR1.

The invention claimed is:

1. A composition in the form of an oil-in-water emulsion comprising 1% to 70% of an oily phase, and an aqueous phase, the composition comprising:
    from 0.1% to 15% by weight of spiculisporic acid relative to the total weight of the composition,
    arginine, wherein arginine is present in an amount that forms a monosalt of spiculisporic acid,
    at least one UV-screening agent and optionally one additive chosen from odorous volatile materials, fillers, dyestuffs, moisturizers, antiwrinkle or antiaging agents, desquamating agents, antioxidants, active agents for stimulating the synthesis of dermal and/or epidermal macromolecules, dermo-decontracting agents, depigmenting agents and deodorants, and mixtures thereof,
    wherein the composition is free of glycol(s) and polyol(s),
    wherein the composition does not comprise any sulfate-based and/or sulfonate-based surfactant.

2. The composition as claimed in claim 1, wherein the composition further comprises at least one base selected from the group consisting of an amino acid chosen from lysine, ornithine, citrulline and histidine.

3. The composition as claimed in claim 1, wherein the amount of arginine ranges from 0.1% to 20% by weight relative to the total weight of the composition.

4. The composition as claimed in claim 1, wherein the oily phase is present in an amount of 5% to 70% by weight relative to the total weight of the composition.

5. The composition as claimed in claim 1, wherein it comprises at least one hydrophilic gelling agent as thickener.

6. The composition as claimed in claim 5, wherein the hydrophilic gelling agent is xanthan gum.

7. The composition as claimed in claim 1, wherein the composition comprises from 0.0001% to 30% of at least one odorous volatile material chosen from essential oils and fragrancing substances.

8. The composition as claimed in claim 7, wherein said UV-screening agent is lipophilic.

9. A nontherapeutic cosmetic makeup, care, hygiene and/or cleansing process comprising a step of applying the composition as claimed in claim 1 to said keratin materials.

10. A nontherapeutic cosmetic process for protecting keratin materials against atmospheric pollutant compounds comprising a step of applying the composition as claimed in claim 1 to said keratin materials.

11. The process as claimed in claim 10, for protecting keratin materials against disorders caused by atmospheric pollutant compounds, said disorders being chosen from greasy skin, skin dehydration, desquamation impairment, a decrease in squalene, a decrease in vitamin E, pigmentation and an increase in lactic acid.

12. The nontherapeutic cosmetic process of claim 10, wherein the atmospheric pollutant compounds are chosen from carbon black, carbon oxides, nitrogen oxides, sulfur oxides, hydrocarbon-based compounds, volatile organic compounds, heavy metals, PM2.5 and PM10 fine particles, and mixtures thereof.

13. The composition according to claim 1, wherein the composition is free of esters of fatty acid.

* * * * *